(12) United States Patent
Topping et al.

(10) Patent No.: US 9,855,396 B2
(45) Date of Patent: Jan. 2, 2018

(54) EMERGENCY TRACHEOTOMY DEVICE

(71) Applicant: Event Horizon Limited, London (CA)

(72) Inventors: Ronald Topping, London (CA);
Russell Craig Inger, Onkaparinga Hills (AU)

(73) Assignee: Event Horizon Limited, London (CA)

( * ) Notice: Subject to any disclaimer, the term of this patent is extended or adjusted under 35 U.S.C. 154(b) by 0 days.

(21) Appl. No.: 15/063,800

(22) Filed: Mar. 8, 2016

(65) Prior Publication Data

US 2016/0184543 A1 Jun. 30, 2016

Related U.S. Application Data

(63) Continuation of application No. PCT/CA2014/050911, filed on Sep. 23, 2014.

(60) Provisional application No. 61/881,100, filed on Sep. 23, 2013.

(51) Int. Cl.
*A61M 16/04* (2006.01)
*A61B 17/34* (2006.01)

(52) U.S. Cl.
CPC ..... *A61M 16/0472* (2013.01); *A61B 17/3415* (2013.01); *A61B 17/3494* (2013.01); *A61M 16/0497* (2013.01); *A61M 2205/58* (2013.01); *A61M 2209/088* (2013.01)

(58) Field of Classification Search
CPC .......... A61M 16/0472; A61M 16/0497; A61B 17/3494; A61B 17/3415
USPC .................................................... 128/207.14
See application file for complete search history.

(56) References Cited

U.S. PATENT DOCUMENTS

| 3,991,765 A | 11/1976 | Cohen |
| 4,325,366 A | 4/1982 | Tabor |
| 4,520,810 A | 6/1985 | Weiss |
| 4,556,059 A | 12/1985 | Adamson |
| 4,622,968 A | 11/1986 | Persson |
| 5,320,608 A * | 6/1994 | Gerrone ............. A61B 17/3417 604/117 |
| 7,169,129 B2 | 1/2007 | Gooden |

(Continued)

FOREIGN PATENT DOCUMENTS

| CN | 2032043 | 2/1989 |
| GB | 2428200 | 1/2007 |
| WO | 2009/102941 | 8/2009 |

*Primary Examiner* — (Jackie) Tan-Uyen T Ho
*Assistant Examiner* — Margaret Luarca
(74) *Attorney, Agent, or Firm* — Robert A. H. Brunet; Brunet & Co. Ltd.

(57) ABSTRACT

A tracheotomy device has a housing configured to guide the device to an appropriate location in a suprasternal notch of a subject and a hollow penetrator associated with the housing. The penetrator resiliently moves from a retracted restrained position to an extended operational position with sufficient force to penetrate a tracheal wall, where the operational position extends a pre-determined distance from the housing. The pre-determined distance is correlated to a distance required to penetrate an anterior side of the tracheal wall without penetrating a posterior side of the tracheal wall. An actuator associated with the housing and the penetrator for releasing the penetrator is configured for use in one hand. The device is simple and disposable and may be used by unskilled caregivers to successfully and safely perform a tracheotomy on a subject with a blocked airway.

23 Claims, 9 Drawing Sheets

(56) References Cited

U.S. PATENT DOCUMENTS

| | | |
|---|---|---|
| 7,267,124 B1* | 9/2007 | Roberson, Jr. .... A61M 16/0472 128/207.29 |
| 7,373,939 B1 | 5/2008 | DuBois et al. |
| 2005/0039755 A1* | 2/2005 | Gooden ............ A61M 16/0472 128/207.14 |
| 2008/0015639 A1* | 1/2008 | Bjork .................... A61B 17/17 606/240 |
| 2008/0029088 A1 | 2/2008 | Freitag |
| 2008/0188947 A1 | 8/2008 | Sanders |
| 2008/0295848 A1 | 12/2008 | Karling et al. |
| 2010/0275911 A1 | 11/2010 | Arlow et al. |
| 2011/0220116 A1* | 9/2011 | Lowenstein ........ A61M 16/044 128/207.14 |
| 2012/0211006 A1 | 8/2012 | Gill et al. |
| 2012/0298102 A1 | 11/2012 | Levitan |

* cited by examiner

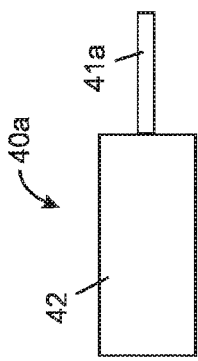
Fig. 5
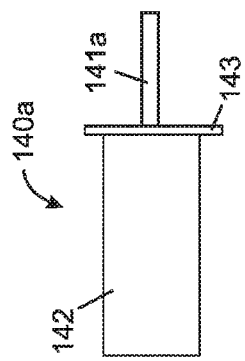
Fig. 6
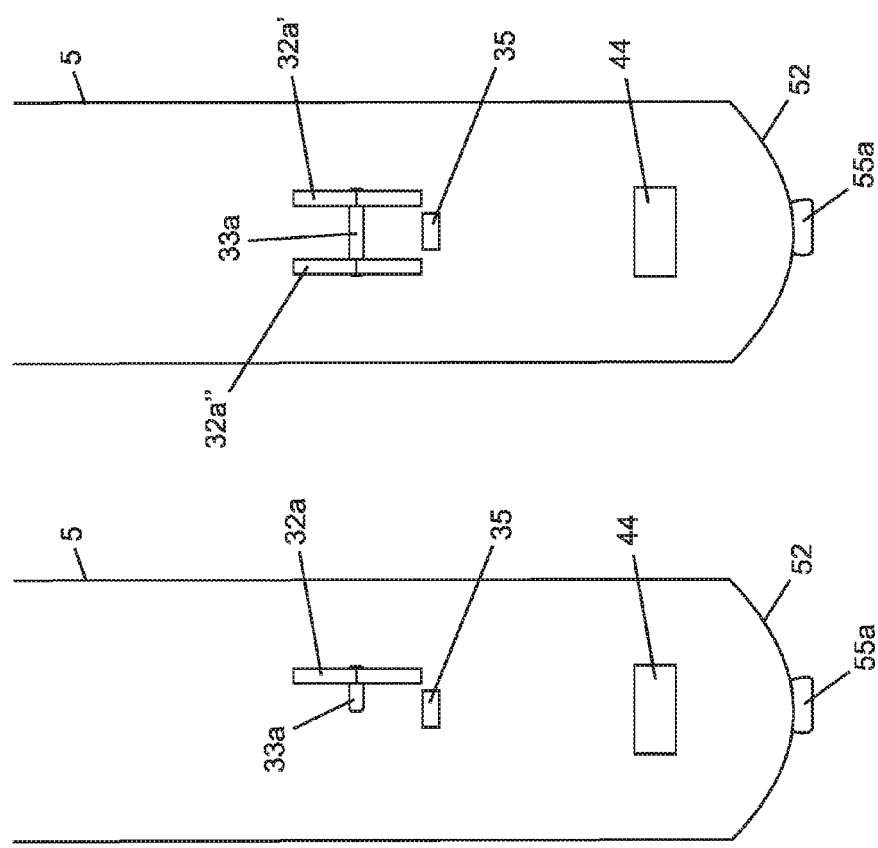
Fig. 4
Fig. 3

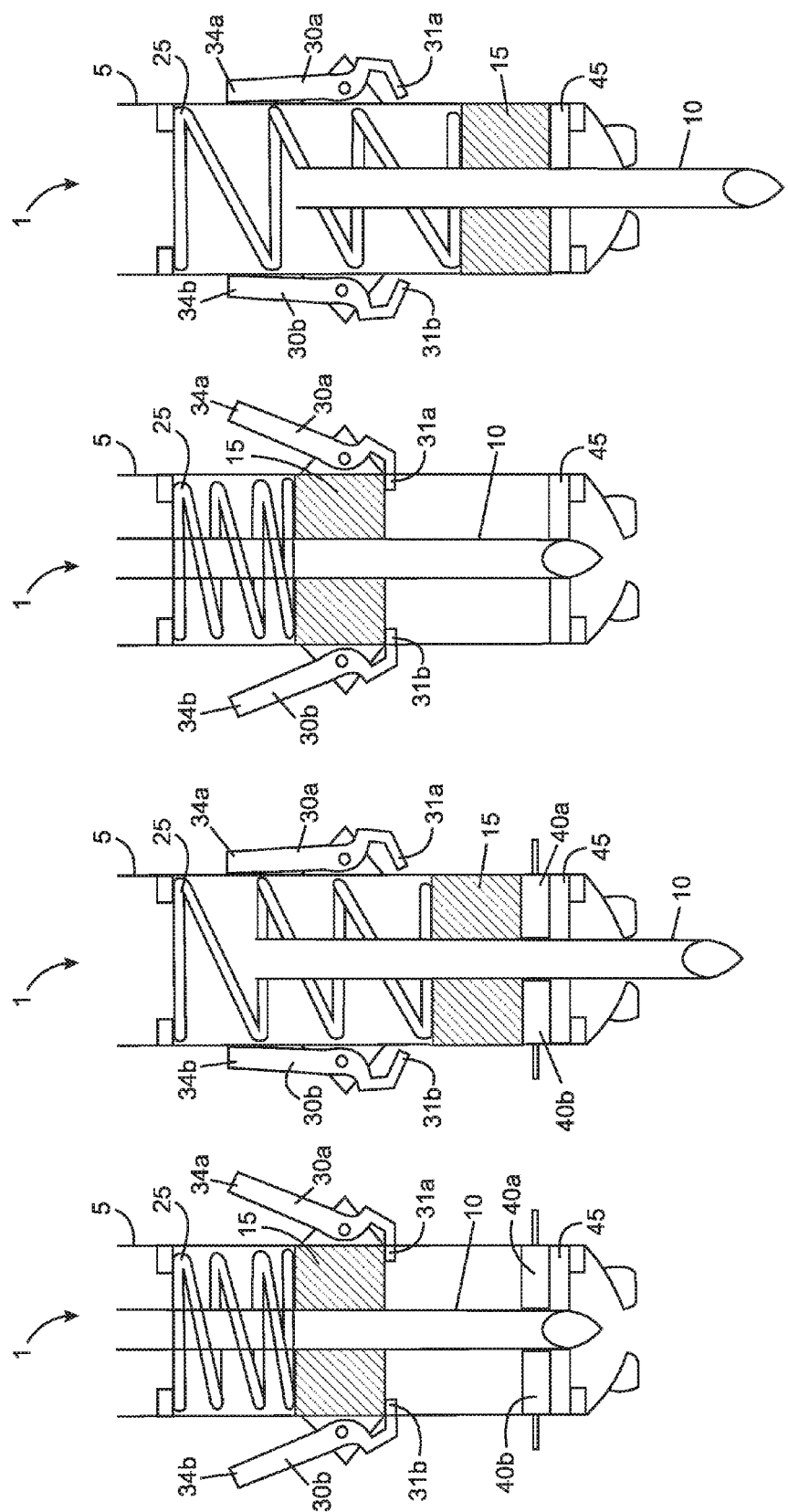

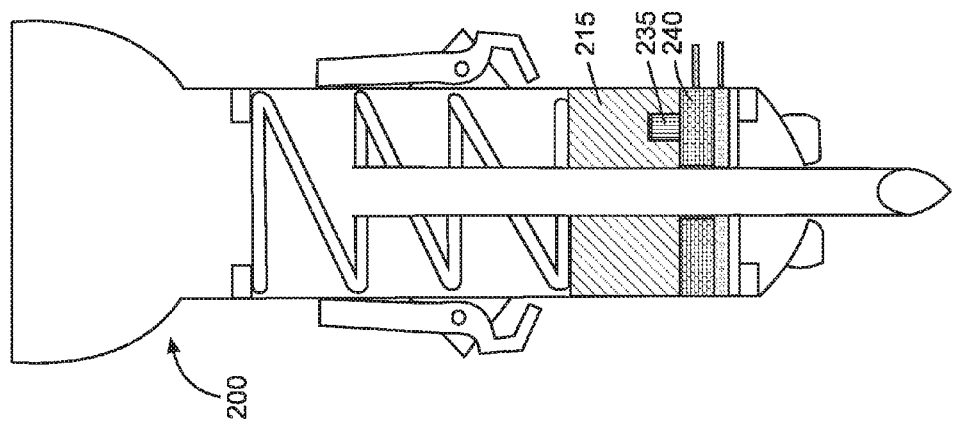
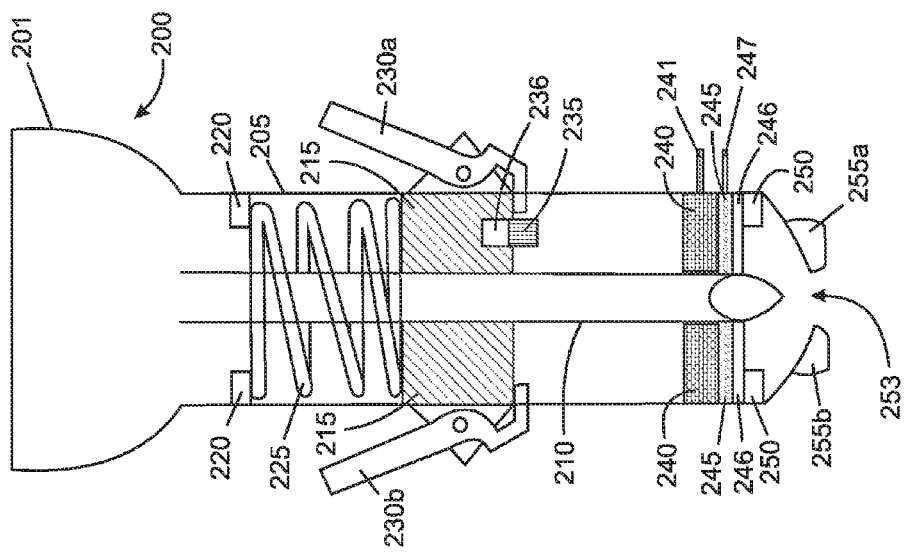

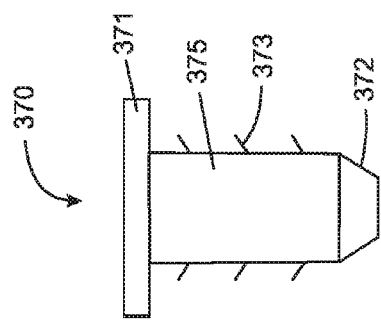
Fig. 10C
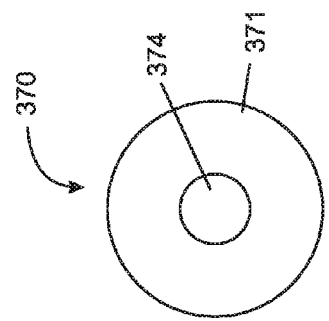
Fig. 10D
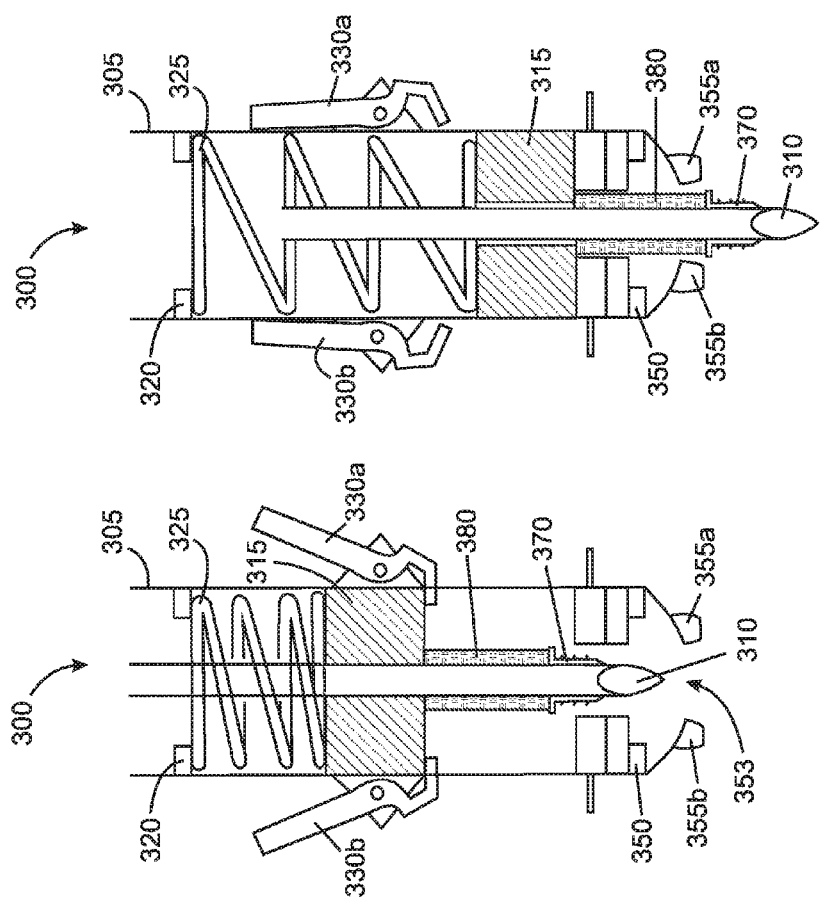
Fig. 10B
Fig. 10A

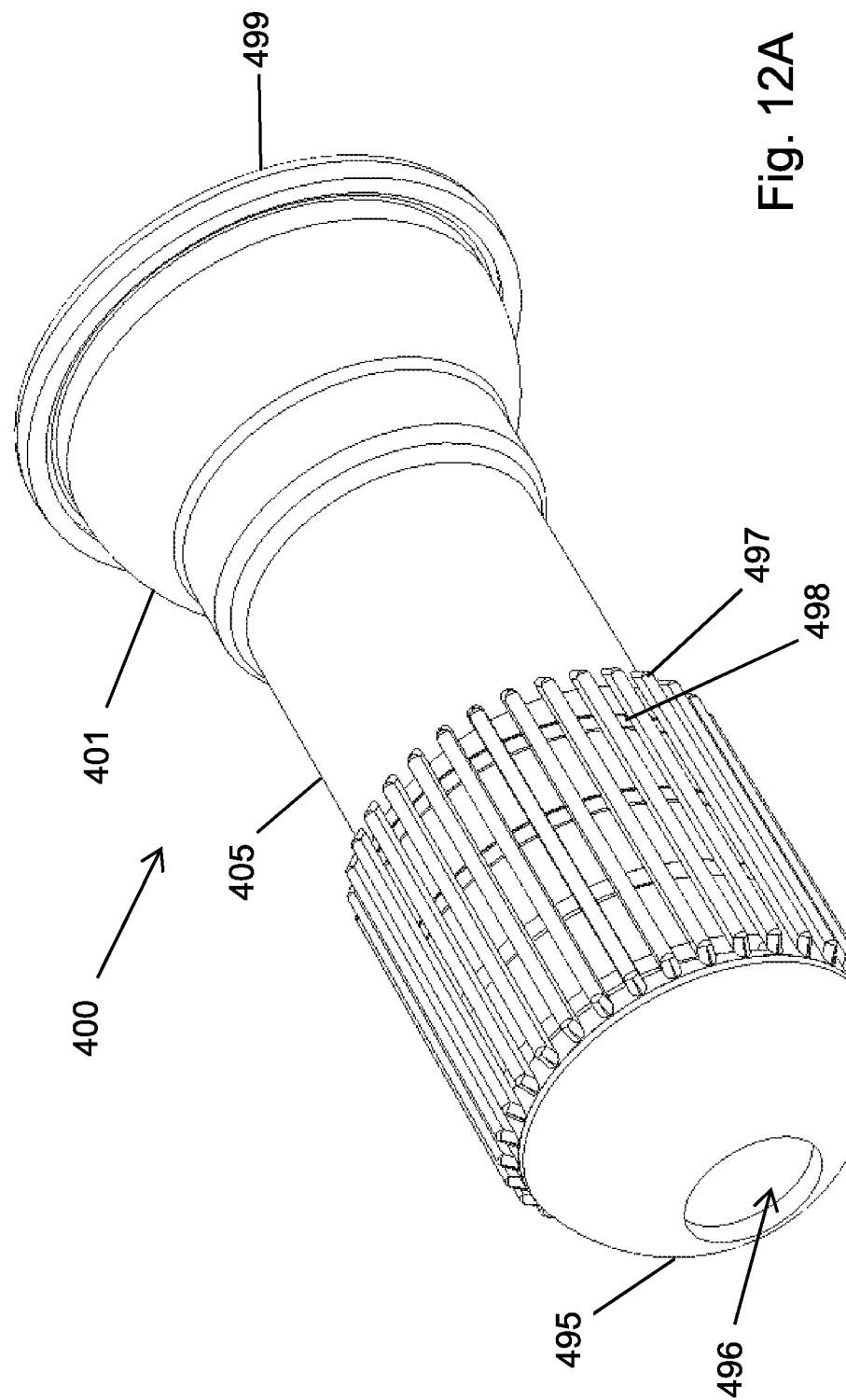

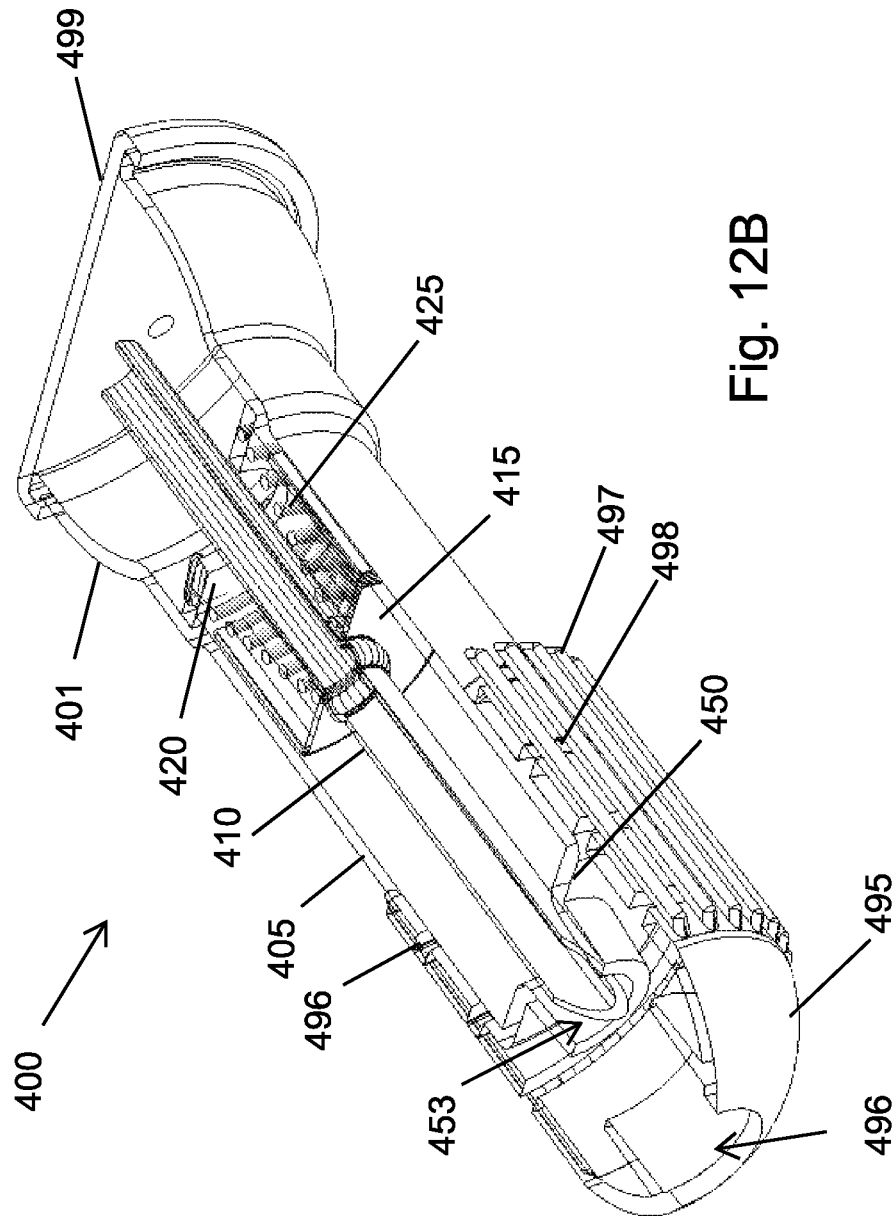

EMERGENCY TRACHEOTOMY DEVICE

CROSS-REFERENCE TO RELATED APPLICATIONS

This application is a continuation of International Patent Application PCT/CA2014/050911, filed Sep. 23, 2014, which claims the benefit of U.S. patent application No. 61/881,100, filed Sep. 23, 2013, the entire contents of which are incorporated herein by reference.

FIELD OF THE INVENTION

The present invention relates to medical devices, in particular to devices for performing emergency tracheotomies.

BACKGROUND OF THE INVENTION

An obstruction in a person's trachea can cause death from asphyxiation, often within minutes before medical help can arrive. When back slaps or the Heimlich maneuver cannot dislodge the obstruction, it may be necessary to perform a tracheotomy. A tracheotomy involves inserting a hollow tube into the trachea below the obstruction so that the person can breathe freely through the tube. Because the trachea is surrounded by stiff cartilaginous material, a scalpel, trocar or other cutting instrument is required to make an incision in the trachea between the cartilaginous rings. This can be difficult without specific knowledge, so tracheotomies traditionally require medical knowledge to perform successfully and safely. Given that the time for trained emergency services personnel to arrive after a subject has begun to choke often exceeds the survival time that someone can survive without breathing, any attempt to save the subject's life must be considered. Therefore, if trained medical personnel are not present, then it would be useful to have a simple emergency tracheotomy device that can be used safely and successfully by the general public with little or no training. Further, to reduce the possibility of contamination and for simplicity, such an emergency device should be simple to use, inexpensive, sterilizable and amenable to single-use with disposal after use.

SUMMARY OF THE INVENTION

There is provided a tracheotomy device comprising: a housing configured to guide the device to an appropriate location in a suprasternal notch of a subject; a hollow penetrator associated with the housing, the penetrator resiliently moveable from a retracted restrained position to an extended operational position with sufficient force to penetrate a tracheal wall, the operational position extending a pre-determined distance from the housing, the pre-determined distance correlated to a distance required to penetrate an anterior side of the tracheal wall without penetrating a posterior side of the tracheal wall; and, an actuator associated with the housing and the penetrator and configured for use in one hand for releasing the penetrator to be resiliently moved from the restrained position to the operational position.

There is further provided a kit comprising a device of the present invention and instructions for use of the device for performing a tracheotomy.

There is further provided a method of performing a tracheotomy comprising positioning a device of the present invention in a suprasternal notch of a subject, and actuating the actuator to release the penetrator into a trachea of the subject.

The penetrator preferably comprises a hollow sharp blade that can penetrate skin and the tracheal wall of the subject. The penetrator may be elongated, for example a hollow needle, scalpel or trocar. Hollow trocars are particularly preferred. The penetrator may comprise any medically approved material, for example stainless steel, and is preferably sterilizable.

The penetrator is resiliently moveable from a retracted restrained position to an extended operational position with sufficient force to penetrate the tracheal wall. Preferably, the penetrator cannot then be reset back to the retracted restrained position to reduce the possibility that the device will be reused, since reuse could increase the chance of infecting future subjects with pathogens. Preferably, a biasing member is employed to provide the resilient movement and penetrating force. The biasing member may be, for example, a spring. Springs include, for example, leaf springs, torsion springs, compression springs and the like. Compression springs are particularly preferred.

The penetrator is associated with a housing. The penetrator may sit within or outside the housing, however, it is preferable that the penetrator is within the housing to reduce the possibility of accidentally causing injury with the penetrator. When the penetrator is in the retracted restrained position it is preferably fully within the housing so that no part of the penetrator is exposed. The housing is preferably a hollow tube with the penetrator housed coaxially within the tube. The tube may have a proximal end and a distal end. The distal end may be configured for placement in the suprasternal notch and may have a discharge aperture through which the penetrator can fully or partially extend when resiliently moved from the restrained position to the operational position. The proximal end of the housing may be configured for blowing air through the penetrator, optionally with the aid of a mouthpiece. The mouthpiece may be unitized with the housing or a separate piece that can be inserted on to the proximal end of the housing. The penetrator may be associated with a sealing element to seal a space between the penetrator and the housing to ensure that air blown into the device passes through penetrator.

The housing preferably comprises an inexpensive material, for example a plastic. The material is preferably moldable to form a one-piece or unitized structure and is preferably sterilizable. A one-piece structure provides for more economical construction and assembly and simplifies sterilization of the device. The housing may be opaque, transparent or translucent. A transparent or translucent housing facilitates observing the condition of the elements inside the housing, for example determining the status of a usage indicator.

The housing is configured to guide the device to an appropriate location in a suprasternal notch of a subject. Preferably, the penetrator is positioned above tissue between cartilaginous rings of the trachea. Therefore, the housing may comprise guide elements that naturally seat themselves between the cartilaginous rings and are configured on the housing to align the penetrator over the tissue between the cartilaginous rings rather than over the cartilaginous rings themselves. The guide elements may be further configured to reduce slippage of the device during actuation of the penetrator. In one embodiment, the housing may comprise spaced-apart protrusions configured to sit between cartilaginous rings of the trachea to guide the penetrator to a position above tissue between the cartilaginous rings when the device is placed in the suprasternal notch.

The housing may further comprise a securement structure for securing the device to the subject when the device is in operation. In one embodiment, the securement structure comprises one or more connections on the housing to which a tying feature, for example a strap, a cord, a string, a chain, etc., may be secured. The tying feature may be looped around the subject's neck and tightened sufficiently to hold the device in place in the suprasternal notch. In another embodiment, the securement structure may comprise a self-adhesive pad that binds sufficiently strongly to skin of the subject that it will not release too easily. When the housing comprises a tube, the self-adhesive pad is preferably located on the distal end of the housing, preferably as a ring that surrounds the discharge aperture.

An actuator is associated with the housing and the penetrator and is configured for use in one hand for releasing the penetrator to be resiliently moved from the restrained position to the operational position. The actuator preferably comprises a depressible structure disposed on a side of the housing whereby pressing the actuator applies a lateral force relative to the direction of motion of the penetrator. The lateral force releases the penetrator to be resiliently moved from the restrained position to the operational position to puncture the skin and tracheal wall to create an opening in the tracheal wall. Depressing the actuator with a lateral force to actuate the penetrator reduces the chance of an inexperienced user bearing down on the device during actuation. Preferably, the actuator comprises two depressible structures disposed on opposed sides of the housing and configured to be simultaneously depressed by one hand, for example by pinching the depressible structures on the housing with thumb and forefinger of one hand. Using two opposed depressible structures advantageously reduces the risk of laterally displacing the device when the penetrator is activated. In one embodiment, the penetrator is restrained in the retracted position by a resiliently deflectable restraint, and the depressible structure is in abutting contact with the resiliently deflectable restraint. Depressing the depressible structure or structures deflects the restraint to release the penetrator for resilient movement to the operational position.

The device preferably comprises a depth selector for selecting the distance that the penetrator moves, and therefore selecting the depth into the subject's body to which the penetrator will go. This is important for reducing the possibility that the penetrator will penetrate the posterior wall of the trachea. It is desired for the penetrator to fully penetrate the anterior wall of the trachea, but penetrating the posterior wall could lead to complications causing death of the subject. While the device may be designed to permit selection of various depths positions, it is preferable for simplicity to have only two or three pre-set positions, one for a human adult, one for a human child, and possibly one for an oversized human adult. The depths to which the penetrator must penetrate in each of these cases are sufficiently different that different pre-determined distances are warranted. The pre-set positions may be marked with indicia to indicate the age/size group for which the position is suited. The indicia may be printed or engraved on the housing and/or ring. The indicia may comprise words, pictures or both.

The depth selector can function by altering the position of the penetrator in relation to the housing, by altering the length of the housing or by altering the position of a stop inside the housing. Preferably, the depth selector adjusts a position of a stop that stops the penetrator from extending beyond the pre-determined distance. The stop may be a projection in the housing that may be moved longitudinally in relation to the direction of motion of the penetrator, or that may be removed from inside the housing.

In one embodiment, the depth selector comprises a rotatable ring around an exterior of the housing. The ring may be rotatatable on a threaded surface so that rotation of the ring moves the ring axially along the housing. Movement of the ring axially along the house may serve to lengthen the housing. The ring may comprise a projection projecting into the housing that engages the penetrator to stop the penetrator from extending beyond the pre-determined position. The penetrator may comprise a corresponding projection for engagement with the projection on the ring.

In another embodiment, the depth selector comprises a first pre-set position defined by a first stop in the housing, which extends through an aperture in the housing and which is configured to be removable from the aperture and therefore from the inside of the housing, for example by pulling the first stop out of the aperture. A pull tab attached to the first stop and extending outside the housing may be used to pull the first stop out of the housing. A second pre-set position defined by a second stop located inside the housing and farther toward the distal end of the housing sets the pre-determined distance once the first stop is removed. The first stop may define the pre-determined distance for a human child while the second stop may define the pre-determined distance for a human adult.

In an alternative embodiment, the device may have only one pre-set position specific for a particular age or size group, and several different models of the device constructed, each for use with a different age or size group.

The device may comprise a usage indicator that indicates whether the device has been used or is still in a ready-to-use state. This is particularly important as a safety measure to ensure sterility of the device, especially for disposable devices. It may be possible to reload the penetrator after use by pushing the penetrator back into the housing and re-setting the actuator, which comprises sterility and therefore safety. Thus, a non-re-settable usage indicator would be beneficial. The usage indicator may be a visual indicator located inside the housing and visible either through a window in the housing or by virtue of the housing being transparent or translucent. In one embodiment, the usage indicator may be a flag, preferably colored with a bright color (e.g. green, red, orange and the like), whereby operation of the device changes the location of the flag relative to another element of the device.

In a particularly preferred embodiment, a disposable tracheotomy device comprises: a spring-loaded hollow penetrator housed within a hollow tube, the penetrator resiliently moveable by a spring from a retracted restrained position to an extended operational position with sufficient force to penetrate a tracheal wall, the operational position extending a pre-determined distance from a distal end of the hollow tube, the pre-determined distance correlated to a distance required to penetrate an anterior side of the tracheal wall without penetrating a posterior side of the tracheal wall; spaced-apart protrusions on the distal end of the hollow tube configured to sit between cartilaginous rings of a trachea to guide the penetrator to a position above tissue between the cartilaginous rings when the device is placed in a suprasternal notch of a subject; and, two depressible actuators disposed on opposed sides on the housing and configured for use in one hand for releasing the spring-loaded penetrator by action of lateral force relative to direction of motion of the penetrator to permit the spring to resiliently move the penetrator from the restrained position to the operational position.

A kit of the present invention comprises the device of the present invention together with instructions for use of the device for performing a tracheotomy. The instructions may take the form of printed matter, for example, text, illustrations or both. The device is preferably sterilized and then shrink wrapped in a sealed package to prevent contamination. The instructions may be printed on the shrink wrap or accompany the shrink wrapped device in another packaging material.

To use the device in an emergency setting after backslapping and the Heimlich maneuver have failed to dislodge an obstruction in a choking subject's trachea, the subject is laid on his/her back and any neck-covering clothing is removed. The subject is generally unconscious at this point. The user reviews the instructions accompanying the device if not already familiar with them. The device is then unwrapped, the appropriate pre-set distance is selected and the device is placed in the hollow of the subject's neck, i.e. in the suprasternal notch. The guide elements naturally position the device in the correct place in the suprasternal notch. The actuator is then pressed to release the penetrator which extends out under the influence of the bias to penetrate the skin and trachea. The subject can now breathe through the hollow penetrator, or air can be blown into the subject's lungs through the hollow penetrator. The device is secured to the subject until trained medical personnel arrive.

The device of the present invention is preferably a single-use device that may be disposed of after use. It is simple to use so that unskilled people or people with only basic first aid training can successfully and safely perform an emergency tracheotomy. The device is particularly useful in military applications, schools, airplanes, restaurants, and similar venues where the likelihood of someone choking on an obstruction is higher. Further, people who are afraid, unwilling or too nervous to push a hollow blade into a subject's neck are instead able to simply position the device on the subject's neck and release the penetrator by simply depressing an actuator. The device is preferably used when the subject has lost consciousness after the use of back-slapping and the Heimlich maneuver has been unsuccessful at clearing a blockage in the trachea.

Further features of the invention will be described or will become apparent in the course of the following detailed description. It should be understood that each feature described herein may be utilized in any combination with any one or more of the other described features, and that each feature does not necessarily rely on the presence of another feature except where evident to one of skill in the art.

BRIEF DESCRIPTION OF THE DRAWINGS

In order that the invention may be more clearly understood, embodiments thereof will now be described in detail by way of example, with reference to the accompanying drawings, in which:

FIG. 3 depicts a schematic drawing of the tracheotomy device of FIG. 1 rotated 90-degrees about a vertical axis in which release clips and child setting stops are removed;

FIG. 4 depicts a schematic drawing of the tracheotomy device of FIG. 3 showing an alternative embodiment of a release clip mount;

FIG. 5 depicts a side view of a first embodiment of a child setting stop;

FIG. 6 depicts a side view of a second embodiment of a child setting stop;

FIG. 7A depicts the tracheotomy device of FIG. 1 set for a child and in a ready-to-use state;

FIG. 7B depicts the tracheotomy device of FIG. 7A in an extended used state;

FIG. 8A depicts the tracheotomy device of FIG. 1 set for an adult and in a ready-to-use state;

FIG. 8B depicts the tracheotomy device of FIG. 8A in an extended used state;

FIG. 9A depicts a schematic drawing of another embodiment of a tracheotomy device in accordance with the present invention showing internal and external structures;

FIG. 9B depicts the tracheotomy device of FIG. 9A in an extended used state;

FIG. 10A depicts a schematic drawing of another embodiment of a tracheotomy device in accordance with the present invention showing internal and external structures in a ready-to-use state;

FIG. 10B depicts the tracheotomy device of FIG. 10A in an extended used state;

FIG. 10C depicts a magnified side view of a trocar sleeve used in the tracheotomy device of FIG. 10A;

FIG. 10D depicts a magnified top view of a trocar sleeve used in the tracheotomy device of FIG. 10A;

FIG. 12A depicts another embodiment of a tracheotomy device in accordance with the present invention in perspective view; and, FIG. 12B depicts the embodiment of FIG. 12A in a cross-sectional perspective view.

DESCRIPTION OF PREFERRED EMBODIMENTS

Figure 1:
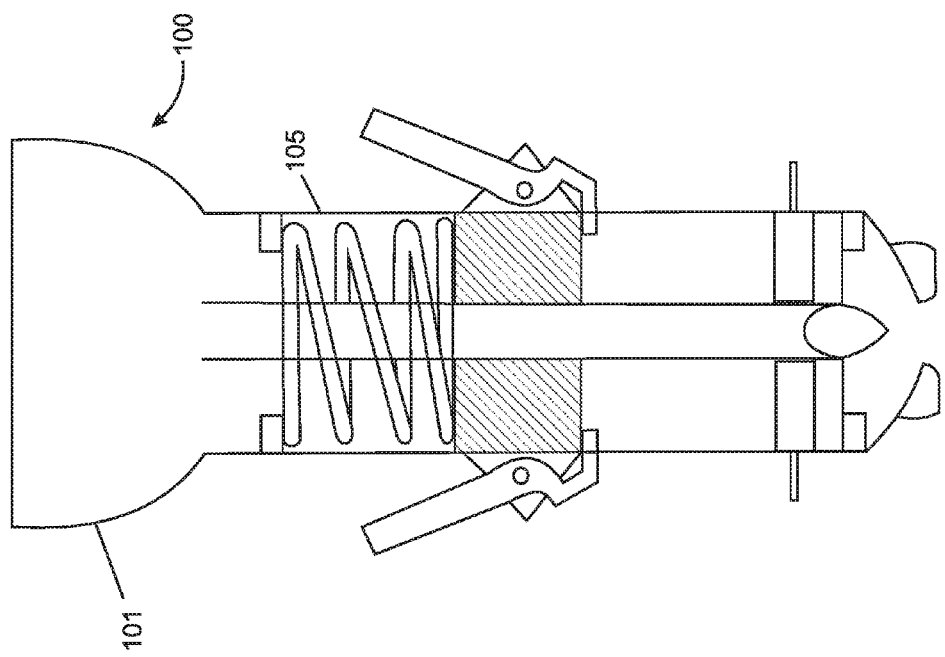
FIG. 1 depicts a schematic drawing of a tracheotomy device in accordance with the present invention showing internal and external structures.

Referring to FIG. 1, a tracheotomy device 1 includes a housing comprising a hollow open-ended tube 5 containing a trocar 10 supported in a trocar seal and support 15. The tube 5 may have any suitable cross-sectional shape, for example circular, rectangular, square, hexagonal and the like. The trocar seal and support 15 comprises an annular sealing member having a through aperture through which the trocar 10 extends, the sealing member forming a seal with an outer surface of the trocar 10 so that the trocar 10 cannot move translationally in the trocar seal and support 15. The trocar seal and support 15 is slidably engaged within the tube 5. Thus, the trocar 10 moves with the trocar seal and support 15 when the device 1 is activated. The seal may be a friction seal or an adhesive seal.

The tube 5 comprises spring retainer 20 inside and proximate a proximal end of the tube 5. The spring retainer 20 may be an annular protrusion fully or partially around an inner circumference of the tube 5 or it may be two or more separate protrusions extending into the tube 5 from an inner wall of the tube 5. A coiled spring 25 is located between the spring retainer 20 and the trocar seal and support 15. FIG. 1 shows the device in a ready-to-use state so the coiled spring 25 is compressed between the spring retainer 20 and the trocar seal and support 15 biasing the trocar seal and support 15 toward a distal end of the tube 5. Seal engagement portions 31a, 31b of release clips 30a, 30b engage a bottom surface of the trocar seal and support 15 to prevent the coiled spring 25 from moving the trocar seal and support 15 toward the distal end of the tube 5. The release clips 30a, 30b are pivotally mounted on release clip mounts 32a, 32b through pivot pins 33a, 33b (e.g. rivets). The release clip mounts 32a, 32b comprise outwardly extending flanges having through apertures for accepting the pivot pins 33a, 33b. The pressure exerted on the seal engagement portions 31a, 31b of the release clips 30a, 30b by the trocar seal and support 15 as a result of the force exerted by the coiled spring 25 is sufficient to prevent pivoting of the release clips 30a, 30b unless significant force is applied to lever arms 34a, 34b of the release clips 30a, 30b. The lever arms 34a, 34b are configured to be actuated simultaneously by one hand of a person using the device 1. For example, the two lever arms 34a, 34b may be depressed simultaneously by gripping the device 1 between the thumb and forefinger of one hand such that one lever arm is engaged with the thumb and the other lever arm is engaged with the forefinger. Squeezing the thumb and forefinger together would simultaneously depress the two lever arms 34a, 34b thereby activating the device 1.

Proximate the distal end of the tube 5 are child setting stops 40a, 40b. The child setting stops 40a, 40b stop movement of the trocar seal and support 15 and therefore stop movement of the trocar 10 after the device 1 is activated. The child setting stops 40a, 40b are positioned and sized in relation to a length of the trocar 10 to stop movement of the trocar seal and support 15 when the trocar 10 reaches an extended position appropriate for a trachea of a child. If the device 1 is to be used on an adult, the child setting stops 40a, 40b may be removed through apertures in the side walls of the tube 5 (see FIG. 3). The child setting stops 40a, 40b comprise pull tabs 41a, 41b, which allow removal of the child setting stops 40a, 40b from the inside of the tube 5. Applying a lateral force to the pull tabs 41a, 41b results in pulling the child setting stops 40a, 40b out through apertures in the side walls of the tube 5. In a variation, only one child setting stop may be used on one side of the trocar as one stop would be sufficient to arrest the movement of the trocar seal and support. Some variations of child setting stops are illustrated in FIG. 5 and FIG. 6.

Adult setting stop 45 is provided inside the tube 5 distally from the child setting stops 40a, 40b. The adult setting stop 45 is positioned and sized in relation to the length of the trocar 10 to stop movement of the trocar seal and support 15 when the trocar 10 reaches an extended position appropriate for a trachea of an adult. The adult setting stop 45 may be a protrusion fully or partially around the inner circumference of the tube 5 or it may be two or more separate protrusions extending into the tube 5 from the inner wall of the tube 5. If the device 1 is to be a three setting device rather than a two setting device, the adult setting stop 45 may be constructed in a manner similar to the child setting stops.

The child setting stops 40a, 40b and the adult setting stop 45 should be sized to permit the trocar 10 to pass unimpeded while stopping the trocar seal and support 15 at the appropriate position.

Final retainer 50 is provided inside the tube 5 distally from the adult setting stop 45. The final retainer 50 provides further support to absorb the force generated by the coiled spring 25 when the trocar seal and support 15 is forced against the child setting stops 40a, 40b or the adult setting stop 45. In addition, if the adult setting stop 45 is removable, the final retainer 50 may be positioned and sized in relation to the length of the trocar 10 to stop movement of the trocar seal and support 15 when the trocar 10 reaches an extended position appropriate for a trachea of an extra-large adult.

At the distal end of the tube 5, the tube 5 may comprise an inwardly depending surface 52 narrowing to an aperture 53 that is large enough to permit egress of the trocar 10 out of the tube 5 while small enough to ensure that the trocar 10 maintains linear movement as it passes out of the tube 5. The inwardly depending surface 52 comprises alignment tabs 55a, 55b that are positioned, sized and shaped to guide the device 1 naturally to the correct position in a suprasternal notch of a person on which the device 1 is being used. For durability and performance, spring retainer 20, final retainer 50, release clip mounts 32a, 32b and alignment tabs 55a, 55b may be monolithically molded with the tube 5.

Figure 2:
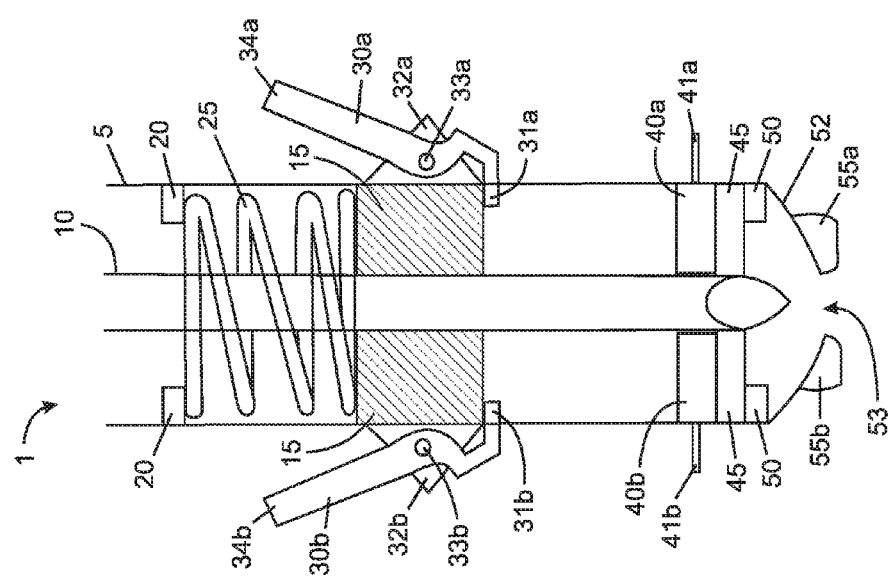
FIG. 2 depicts a schematic drawing of a tracheotomy device in accordance with the present invention having a mouthpiece and showing internal and external structures.

Referring to FIG. 2, a tracheotomy device 100 of generally the same construction as the device of FIG. 1 is shown. The device 100 comprises a mouthpiece 101 at a proximal end of hollow tube 105. The mouthpiece 100 has a larger diameter than the tube 105 and the diameter of the mouthpiece 100 is sized to fit comfortably in a person's mouth. The mouthpiece 100 is shown monolithically molded with the tube 105, but it may alternatively be a separate piece that is fitted on to the tube 105. Friction fittings, mated screw threads, clips or any other suitable structures may be used to fit the mouthpiece to the tube.

FIG. 3 depicts an external surface of the tracheotomy device of FIG. 1 rotated 90-degrees about a vertical axis in which the release clip 30a and the child setting stop 40a are removed. As seen in FIG. 3 with reference to FIG. 1, the tube 5 comprises a through aperture 35 through which the seal engagement portions 31a extends when the device 1 is in the ready-to-use state. When the lever arm 34a of the release clip 30a is depressed with sufficient force toward the tube 5, the release clip 30a pivots on pivot pin 33a mounted on the release clip mount 32a causing the seal engagement portion 31a to slide out of the through aperture 35 thereby releasing the trocar seal and support 15 to move under the force of the coiled spring 25. There is a similar arrangement on the other side of the tube 5 in relation to the release clip 30b. Simultaneously depressing both of the lever arms 34a, 34b of both release clips 30a, 30b permits simultaneous release of the trocar seal and support 15 one both sides of the tube 5 so that the trocar 10 may move in a substantially linear path out of the tube 5 with minimal lateral movement away from the vertical axis. Lateral movement of the trocar 10 is preferably avoided so that the trocar 10 does not jam in the tube 5 and so that the trocar 10 pierces the trachea cleanly between cartilaginous rings of the neck.

FIG. 4 depicts the device of FIG. 3 with an alternative embodiment of the release clip mount 32a. The release clip mount comprises two substantially parallel outwardly extending flanges 32a', 32a'''' having the pivot pin 33a mounted therebetween. Providing an addition outwardly extending flange provides greater durability and better support for the release clips. A similar release clip mount may be present on the other side of the tube 5, although it is possible to use different release clip mounts on each side.

Referring again to FIG. 3, the tube 5 comprises a through aperture 44 proximate the distal end of the tube 5 through which the child setting stop 40a may be removed. There may be a similar arrangement on the other side of the tube 5. Referring to FIG. 5 and FIG. 6, variations of child setting stops are illustrated. In all cases, the width of the child setting stops should be no larger than the width of the through aperture 44 so that the stop may be pulled out through the aperture 44. As shown in FIG. 5, the child setting stop 40a may comprise a rectangular solid portion 42 that extends into the tube 5 through the aperture 44 and a pull tab 41a attached to or integrally formed with the rectangular solid portion 42 that protrudes outwardly from the tube 5. Since the rectangular solid portion 42 rests on the adult setting stop 45 inside the tube 5, no further support is necessarily required. However, it is possible that the child setting stop 40a could move farther inward thereby potentially interfering with movement of the trocar 10. If further surety is required, a child setting stop 140a as illustrated in FIG. 6 may be employed in which a lip 143 is provided between a rectangular solid portion 142 and a pull tab 141a. The lip 143 is located exterior to the tube 5 and is dimensioned larger than the aperture 44 to prevent the rectangular solid portion 142 from migrating farther into the tube 5.

FIG. 7A, FIG. 7B, FIG. 8A and FIG. 8B illustrate the operation of the device 1. FIG. 7A depicts the tracheotomy device 1 in the ready-to-use state for a child, as already described in relation to FIG. 1. When the device 1 is in the ready-to-use state, the trocar 10 is fully within the tube 5. When the lever arms 34a, 34b are depressed simultaneously, the trocar seal and support 15 is released and the coiled spring 25 biasing the trocar seal and support 15 toward the distal end of the tube 5 is allowed to extend thereby driving the trocar seal and support 15 toward the distal end of the tube 5. The trocar 10 is driven with the trocar seal and support 15 as the trocar seal and support 15 slides in the tube 5 until the trocar seal and support 15 abuts the child setting stops 40a, 40b in the extended used state (FIG. 7B). In the extended used state, the trocar 10 now protrudes from the distal end of the tube 5 at a distance appropriate for a tracheotomy on a child. As can be seen in FIG. 7B, the lever arms 34a, 34b are now up against the side wall of the tube 5 and the seal engagement portions 31a, 31b of the release clips 30a, 30b are outside the tube 5. Further, the trocar seal and support 15 abutting the child setting stops 40a, 40b provides for a seal so that air being blown into the tube 5 from the proximal end of the tube 5 can pass through the trocar 10 rather escaping between the inner wall of the tube 5 and an outer edge of the trocar seal and support 15. To further enhance the seal, a sealing element (e.g. an o-ring or a gasket) may be provided on a bottom surface of the trocar seal and support 15. FIG. 8A and FIG. 8B illustrate the same operation except that the tracheotomy device 1 in the ready-to-use state for an adult. It can be seen in FIG. 8A and FIG. 8B that the child setting stops 40a, 40b have been removed so that the trocar seal and support 15 abuts the adult setting stop 45 in the extended used state. Thus, the trocar 10 extends further out from the tube 1 when the device 1 is used for an adult (compare FIG. 8B to FIG. 7B).

Referring to FIGS. 9A-9H, another embodiment of a tracheotomy device 200 is depicted comprising many similar features as the device of FIG. 1 including a housing comprising a hollow open-ended tube 205, a trocar 210, a trocar seal and support 215, a spring retainer 220, a coiled spring 225, release clips 230a, 230b, a final retainer 250, a trocar exit aperture 253 and alignment tabs 255a, 255b. The tracheotomy device 200 is equipped with a mouthpiece 201. The operation of the tracheotomy device 200 is substantially the same as the operation of the tracheotomy device 1 and 100 of FIGS. 1-2.

Figure 9C:
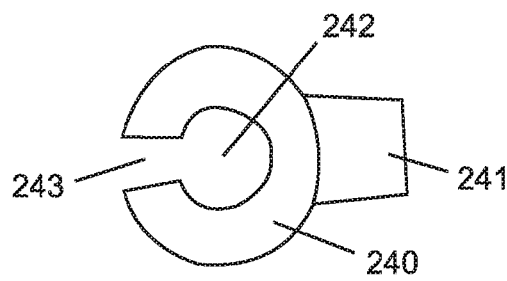
FIG. 9C depicts a schematic drawing of a top view of a child setting stop used in the tracheotomy device of FIG. 9A.

In the tracheotomy device 200 a single-piece child setting stop 240 is provided, the child setting stop 240 comprising a single pull tab 241. A single-piece adult setting stop 245 on which the child setting stop 240 rests is also provided. The adult setting stop 245 also has only one pull tab 247. The design of the setting stops 240, 245 are substantially the same and is described in relation to the child setting stop 240 as depicted in FIGS. 9C-9D. The adult setting stop 245 rests on an extra-large adult setting stop 246. Both the child setting stop 240 and the adult setting stop 245 are removable by pulling on the respective pull tabs 241, 247. The extra-large adult setting stop 246 is not removable and comprises a substantially annular ring resting on the final retainer 250 inside the tube 205. As shown in FIG. 9C, the child setting stop 240 (as well as the adult setting stop 245) comprises a generally annular disc surrounding a central aperture 242 through which the trocar 210 may pass. The generally annular disc has an arc section cut out therefrom to form a slot 243 of sufficient size so that the trocar 210 will pass through the slot 243 when the pull tab 241 of the child setting stop 240 is pulled to remove the child setting stop 240 from the tube 205. FIG. 9E illustrates how a cut-away 249 is disposed in the tube 205 to provide sufficient clearance for the child and adult setting stops 240, 245 to be pulled out of the tube 205. The child and adult setting stops 240, 245 and the cut-away 249 should be sized and constructed so that the setting stops 240, 245 cannot simply fall out of the tube 205, but can be pulled out of the tube 205 without exerting undue force.

Figure 9F:
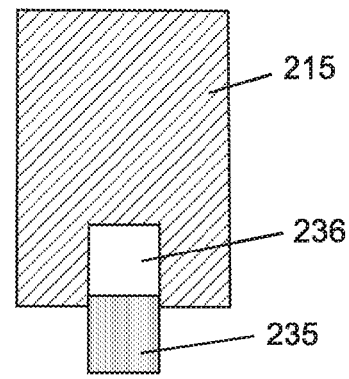
FIG. 9F depicts a side view of a trocar seal and support of the tracheotomy device of FIG. 9A showing a usage flag in an unused position in relation to a recess in the seal and support.
Figure 9D:
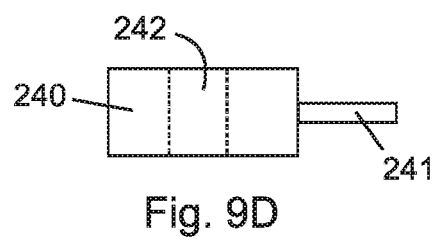
FIG. 9D depicts a schematic drawing of a side view of the child setting stop of FIG. 9C.
Figure 9G:
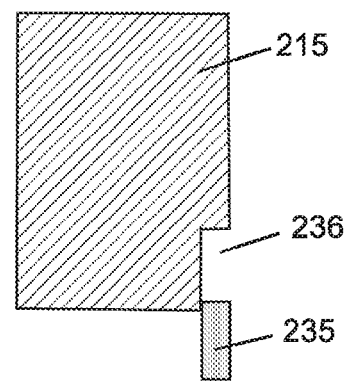
FIG. 9G depicts the trocar seal and support of FIG. 9F rotated 90°.
Figure 9E:
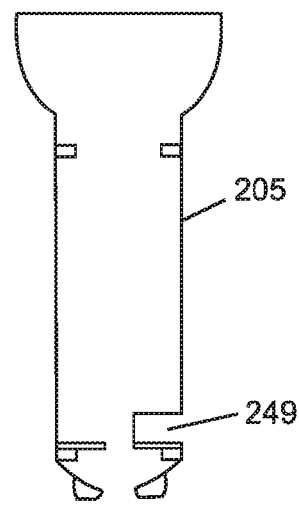
FIG. 9E depicts a schematic drawing of a side view of a tube of the tracheotomy device of FIG. 9A showing a cut-away in the tube to accommodate child and adult setting stops.
Figure 9H:
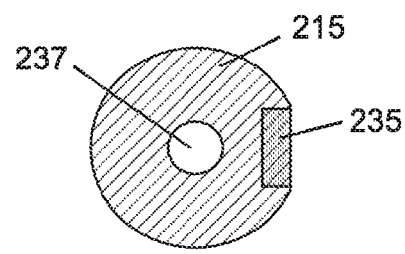
FIG. 9H depicts a bottom view of the trocar seal and support of FIG. 9G.

Referring again to FIGS. 9A-9B as well as to FIGS. 9F-9G, the tracheotomy device 200 also comprises a green usage flag 235 (although other colors may be used) associated with the trocar seal and support 215. The usage flag 235 may comprise plastic, although any suitable material may be employed. When the device 200 is in the ready-to-use state, the usage flag 235 depends downwardly from the trocar seal and support 215, and is visible either through transparent/translucent material of the tube 205 or through a window in the tube 205. The trocar seal and support 215 also comprises a recess 236 so that when the trocar seal and support 215 is driven distally carrying the trocar 210 fixed in aperture 237 of the trocar seal and support 215, the usage flag 235 is driven into the recess 236 by the force of the impact on one of the setting stops, for example the child setting stop 240 as shown in FIG. 9B. Thus, when the device 200 is in the used state, the usage flag 235 does not depend below the trocar seal and support 215. In the event that the trocar 210 is reloaded by forcing the trocar 210 with the trocar seal and support 215 back into the tube 205 and re-setting the release clips 230a, 230b, the usage flag 235 will remain in the recess 236 indicating that the device 200 has already been used.

To provide further security from tampering, the recess 236 may be wholly inside the trocar seal and support 215 except for an exposed bottom into which the usage flag 235 may be driven. Thus, the usage flag 235 would not be visible at all from the sides of the device 200 when the device 200 is in the used state. The visual absence of the usage flag 235 as viewed from the side of the device 200 would then be an indicator that the device 200 has been used.

Referring to FIGS. 10A-10B, another embodiment of a tracheotomy device 300 is depicted comprising many similar features as the device of FIG. 1 including a housing comprising a hollow open-ended tube 305, a trocar 310, a trocar seal and support 315, a spring retainer 320, a coiled spring 325, release clips 330a, 330b, a final retainer 350, a trocar exit aperture 353 and alignment tabs 355a, 355b. The operation of the tracheotomy device 300 is substantially the same as the operation of the tracheotomy device 1 of FIG. 1.

However, the tracheotomy device 300 also comprises features beneficial in the event the device is successfully used on an unconscious subject and the subject subsequently regains consciousness. Upon regaining consciousness, the subject is often prone to coughing, panic and/or other vigorous movement. Such activity may dislodge the device. Thus, the tracheotomy device 300 may further comprise a trocar sleeve 370 around the trocar 310, the trocar sleeve 370 being driven with the trocar 310 when the device 300 is actuated. The trocar sleeve 370 may be driven by a hollow cylindrical spacer 380 between the trocar sleeve 370 and the trocar seal and support 315, the spacer 380 also surrounding the trocar 310. The spacer 380 is driven by the trocar seal and support 315 when the coiled spring 325 is released by activation of the release clips 330a, 330b. Alternatively, the trocar sleeve 370 may be sufficiently long that the trocar seal and support 315 drives the sleeve 370 directly. The trocar sleeve 370 and/or hollow cylindrical spacer 380 may comprise any suitable material, for example plastic.

Referring to FIGS. 10C-10D, the trocar sleeve 370 may be of similar shape to the hollow tube 305, for example cylindrical, and may comprise a sleeve body 375 and a through aperture 374 through the sleeve body 375 through which the trocar 310 extends. The trocar sleeve 370 may comprise a tapered distal edge 372 to facilitate entry into the hole in the trachea created by the trocar 310. The trocar sleeve 370 may also comprise a radially extending flange 371 toward a proximal end of the sleeve 370 to prevent the sleeve 370 from completely entering the hole in the trachea to avoid loss of the sleeve 370 in the subject's trachea. The flange 371 has a larger diameter than the body 375 of so that the flange 371 may engage the surface of the subject's neck around the hole created by the trocar. The sleeve 370 is preferably a monolithic structure.

When the device 300 is actuated, the trocar sleeve 370 is driven into the hole in the trachea created by the trocar 310. In the event the subject regains consciousness and moves vigorously due to coughing, panicking or the like, the trocar 310 may be dislodged from the hole in the trachea and from the through aperture 374 in the trocar sleeve 370, but the trocar sleeve 370 may remain in the hole to keep the hole open. To help prevent the trocar sleeve 370 from also becoming dislodged, sides of the sleeve body 375 may comprise one or more features that allow easy penetration while resisting removal. Such features may comprise one or more protrusions, screw threads, or the like. For example, FIG. 100 depicts radially extending ridges 373 (only one labelled) that are angled toward the proximal end to permit easy penetration into the hole while resisting removal from the hole. The trocar sleeve 370 may be removed by medical personnel when the wound in the trachea is treated. The use of a trocar sleeve may also permit deliberate removal of the trocar, if desired, since the subject could breathe through the sleeve rather than the trocar.

Figure 11:
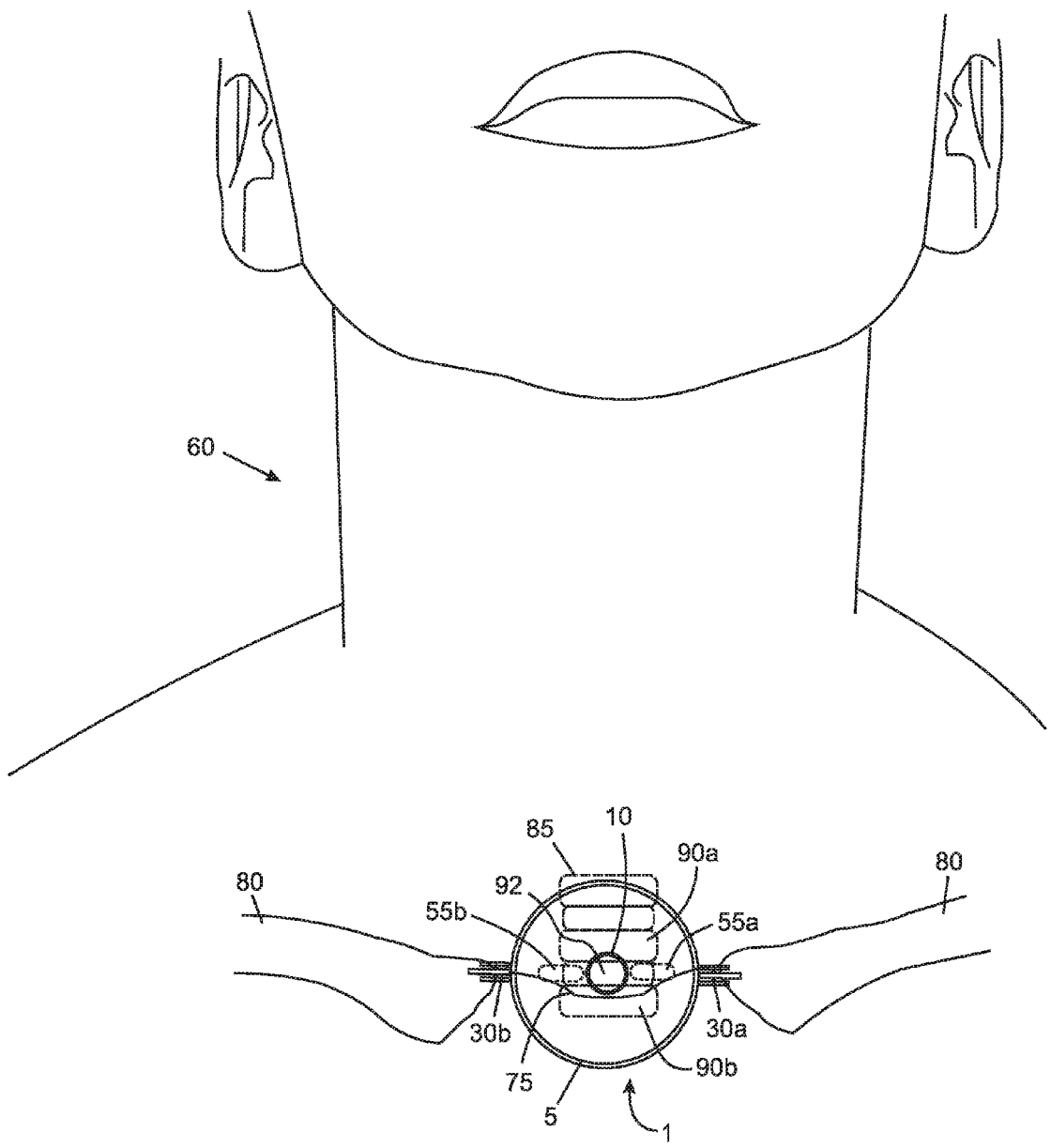
FIG. 11 depicts the tracheotomy device of FIG. 1 positioned above a trachea of a person.

Referring to FIG. 11, in use the tracheotomy device 1 is placed vertically in suprasternal notch 75 of a person 60 lying prone (horizontally). The suprasternal notch 75 is at the top of the sternum (not shown) between the clavicles 80 of the person 60. The suprasternal notch 75 is colloquially known as the hollow of the throat. At the suprasternal notch 75, the device 1 is above a trachea 85 (shown in dashed lines) of the person 60. The alignment tabs 55a, 55b (drawn in stippled lines) guide and position the device 1 in the suprasternal notch 75 such that the trocar 10 is aligned above a gap 92 between two cartilaginous rings 90a, 90b of the trachea 85 to facilitate insertion of the trocar 10 into the trachea 85. Once aligned, the release clips 30a, 30b are actuated and the trocar 10 springs down under the force of the coiled spring to pierce the trachea 85 in the gap 92 between the cartilaginous rings 90a, 90b. With the proper setting (child or adult, or possibly large adult) the trocar 10 will pierce the anterior wall of the trachea 85 without piercing the posterior wall of the trachea 85. With the trocar 10 in the person's trachea, the person may now breathe through the trocar 10, or another person may blow into the proximal end of the tube 5 and thus into the trocar 10 to assist with the person's breathing.

Referring to FIGS. 12A-12B, another embodiment of a tracheotomy device 400 is depicted comprising many similar features as the device of FIG. 1 including a housing comprising a hollow open-ended tube 405, a trocar 410, a trocar support 415, a spring retainer 420, a coiled spring 425, release clips 430a, 430b (not shown in FIGS. 12A-12B), a final retainer 450, and a trocar exit aperture 453. Alignment tabs 455a, 455b (not shown in FIGS. 12A-12B) may also optionally be provided. The tracheotomy device 400 is equipped with a mouthpiece 401 provided with a removable cap 499. The operation of the tracheotomy device 400 is substantially the same as the operation of the tracheotomy device 1 and 100 of FIGS. 1-2.

The housing comprises the mouthpiece 401 at one end, the exit aperture 453 at an opposite end and the hollow tube 405 therebetween. The hollow tube 405 has an exterior threaded surface 498 thereon. The housing further comprises a rotatable ring 497 having an interior threaded surface 496 complementary to the exterior threaded surface 498, a rounded end 495 configured to guide the device 400 to an appropriate location in a suprasternal notch of a subject and a ring aperture 496 aligned with exit aperture 453, thereby permitting passage of the trocar 410 therethrough. The rotatable ring 497 functions as a depth selector by altering the length of the housing. Rotation of the ring 497 moves the ring along the complementary exterior and interior threaded surfaces 498, 496, causing it to extend or retract axially along the hollow tube 405. Movement of the ring axially serves to lengthen or shorten the housing and changes the distance between the exit aperture 453 and the ring aperture 496. Since the trocar 410 protrudes a fixed length from the exit aperture 453, lengthening the housing causes the trocar to protrude through the ring aperture 496 a shorter distance from the rounded end of the ring 497. Since the rounded end 495 of the ring 497 is placed against the throat of the subject, lengthening of the housing effectively causes the trocar 410 to penetrate a shorter distance into the trachea than if the housing were shortened. Thus, depth control of the trocar 410 is possible. Although depth control is infinite, indicia (not shown) on the exterior of the ring 497 can be provided to guide a user of the device 400 to extend the housing to suggested lengths and corresponding trocar penetration depths.

The novel features of the present invention will become apparent to those of skill in the art upon examination of the detailed description of the invention. It should be understood, however, that the scope of the claims should not be limited by the preferred embodiments set forth in the examples, but should be given the broadest interpretation consistent with the specification as a whole.

The invention claimed is:

1. A tracheotomy device comprising:
a housing comprising a hollow tube having a proximal end and a distal end with an inwardly depending guide surface having a central exit aperture, the guide surface configured to guide the device to an appropriate location in a suprasternal notch of a subject for performing a tracheotomy on the subject;
a hollow penetrator associated with the housing, the penetrator resiliently moveable from a retracted restrained position to an extended operational position with sufficient force to penetrate a tracheal wall, the operational position extending a pre-determined distance from the housing through the exit aperture, the pre-determined distance correlated to a distance required to penetrate an anterior side of the tracheal wall without penetrating a posterior side of the tracheal wall; and,
an actuator associated with the housing and the penetrator and configured for use in one hand for releasing the penetrator to be resiliently moved from the restrained position to the operational position, the housing comprising integrally formed spaced-apart protrusions on the guide surface that are positioned, sized and shaped to sit between cartilaginous rings of a trachea of the subject when the guide surface is within the suprasternal notch of the subject, the exit aperture located between the spaced-apart protrusions to guide the penetrator to a position above tissue covering a gap between the cartilaginous rings so that moving the penetrator from the restrained position to the operational position pierces the tissue and causes the penetrator to enter the trachea through the gap between the cartilaginous rings to thereby perform a tracheotomy on the subject.

2. The device according to claim 1, wherein the penetrator is resiliently moveable by a biasing member.

3. The device according to claim 2, wherein the biasing member comprises a spring.

4. The device according to claim 2, wherein the biasing member comprises a compression spring.

5. The device according to claim 1, wherein the actuator comprises a depressible structure disposed on a side of the housing whereby pressing the actuator applies a lateral force relative to direction of motion of the penetrator that releases the penetrator to be resiliently moved from the restrained position to the operational position to create an opening in the tracheal wall.

6. The device according to claim 5, wherein the penetrator is restrained in the retracted position by a resiliently deflectable restraint, and wherein the depressible structure is in abutting contact with the resiliently deflectable restraint, whereby depressing the depressible structure deflects the restraint to release the penetrator for resilient movement to the operational position.

7. The device according to claim 5, wherein the actuator comprises two depressible structures disposed on opposed sides of the housing and configured to be simultaneously depressed by the one hand.

8. The device according to claim 1, further comprising a depth selector for selecting the pre-determined distance.

9. The device according to claim 8, wherein the depth selector comprises first and second stops defining first and second pre-set positions, the first pre-set position selecting a depth appropriate for a human child and the second pre-set position selecting a depth appropriate for a human adult, the first stop extending through an aperture in the housing and configured to be removable from the housing.

10. The device according to claim 8, wherein the depth selector adjusts a position of a stop that stops the penetrator from extending beyond the pre-determined distance.

11. The device according to claim 8, wherein the depth selector comprises a rotatable ring around the housing rotatable between at least first and second positions, the first position selecting a depth appropriate for a human adult and the second position selecting a depth appropriate for a human child.

12. The device according to claim 1, wherein the penetrator comprises a trocar, a needle or a scalpel.

13. The device according to claim 1, wherein the penetrator comprises a hollow trocar.

14. The device according to claim 1, further comprising a usage indicator that indicates whether the device is in a used state or is still in a ready-to-use state, wherein, following use, the usage indicator remains in the used state when the penetrator is re-loaded by forcing the penetrator back into the tube.

15. The device according to claim 1, wherein the housing further comprises a securement structure for securing the device to the subject when the device is in operation.

16. The device according to claim 15, wherein the securement structure comprises a self-adhesive pad that binds to skin of the subject.

17. The device according to claim 1, wherein the penetrator is retained within the housing and is biased from the restrained position where the penetrator is entirely housed within the housing to the operational position where at least a portion of the penetrator protrudes from the discharge aperture.

18. The device according to claim 1, wherein the proximal end of the housing is configured with a mouthpiece for blowing air through the penetrator.

19. The device according to claim 1, further comprising a sleeve around the penetrator, the sleeve moveable with the penetrator to enter the anterior side of the tracheal wall through a hole in the anterior side created by the penetrator penetrating the tracheal wall.

20. The device according to claims 1, configured for a single use.

21. A disposable tracheotomy device comprising:
(a) a spring-loaded hollow penetrator housed within a hollow tube, the penetrator resiliently moveable by a spring from a retracted restrained position to an extended operational position with sufficient force to penetrate a tracheal wall, the operational position extending a pre-determined distance from a distal end of the hollow tube through a central exit aperture, the pre-determined distance correlated to a distance required to penetrate an anterior side of the tracheal wall without penetrating a posterior side of the tracheal wall the distal end having a rounded guide surface configured to guide the device to an appropriate location in a suprasternal notch of a subject for performing a tracheotomy on the subject;
(b) spaced-apart protrusions on the rounded guide surface that are positioned, sized and shaped to sit between cartilaginous rings of a trachea of the subject when the guide surface is within the suprasternal notch of the subject, the exit aperture located between the spaced-apart protrusions to guide the penetrator to a position above tissue covering a gap between the cartilaginous rings so that moving the penetrator from the restrained position to the operational position pierces the tissue and causes the penetrator to enter the trachea through the gap between the cartilaginous rings to thereby perform a tracheotomy on the subject; and, (c) two depressible actuators disposed on opposed sides on the housing and configured for use in one hand for releasing the spring-loaded penetrator by action of lateral force relative to direction of motion of the penetrator to permit the spring to resiliently move the penetrator from the restrained position to the operational position.

22. A kit comprising a device as defined in claim 1 and instructions for use of the device for performing a tracheotomy.

23. A method of performing a tracheotomy comprising: positioning a device as defined in claim 1 in a suprasternal notch of a subject; and, actuating the actuator to release the penetrator into a trachea of the subject.

* * * * *